United States Patent
Force et al.

(10) Patent No.: US 11,805,817 B2
(45) Date of Patent: *Nov. 7, 2023

(54) SPLIT AIRFLOW SYSTEM FOR AN ELECTRICALLY HEATED SMOKING SYSTEM AND METHOD FOR GUIDING AN AIRFLOW INSIDE AN ELECTRICALLY HEATED SMOKING SYSTEM

(71) Applicant: Philip Morris Products S.A., Neuchatel (CH)

(72) Inventors: Eric Force, Bevaix (CH); Oleg Mironov, Neuchatel (CH); Ihar Nikolaevich Zinovik, Peseux (CH); Keethan Dasnavis Fernando, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 214 days.

This patent is subject to a terminal disclaimer.

(21) Appl. No.: 17/245,683

(22) Filed: Apr. 30, 2021

(65) Prior Publication Data

US 2021/0244099 A1    Aug. 12, 2021

Related U.S. Application Data

(63) Continuation of application No. 16/877,464, filed on May 18, 2020, now Pat. No. 11,006,676, which is a (Continued)

(30) Foreign Application Priority Data

Dec. 15, 2014 (EP) ..................................... 14197849

(51) Int. Cl.
*A24F 40/46* (2020.01)
*A24F 40/40* (2020.01)
(Continued)

(52) U.S. Cl.
CPC .............. *A24F 40/46* (2020.01); *A24F 40/40* (2020.01); *A24F 40/485* (2020.01); (Continued)

(58) Field of Classification Search
None
See application file for complete search history.

(56) References Cited

U.S. PATENT DOCUMENTS 9,532,600 B2    1/2017   Thorns
9,555,198 B2    1/2017   Yang
(Continued)

FOREIGN PATENT DOCUMENTS

CN    102014677 A    4/2011
CN    102655773 A    9/2012
(Continued)

OTHER PUBLICATIONS

Office Action issued in Japan for Application No. 2017-529990 dated Feb. 3, 2020 (18 pages). English translation included.
(Continued)

*Primary Examiner* — Phu H Nguyen
(74) *Attorney, Agent, or Firm* — Oblon, McClelland, Maier & Neustadt, L.L.P.

(57) ABSTRACT

A cartridge system is provided, including a liquid storage portion including a housing to hold a liquid aerosol-forming substrate; a mouthpiece having an outlet opening removably connected to a first end of the storage portion; and a heater assembly including an electrical heating element to heat the substrate to form an aerosol, and a porous capillary material having a first face contacting part of the heating element and to convey the substrate to the heating element by capillary action, the heating element disposed across the first face of the material, the liquid storage portion disposed at a first side of the heater assembly and a first airflow channel disposed
(Continued)

at a second side of the assembly and defining an airflow path directed at a center of the heating element, and part of a second airflow channel extending to the outlet opening via a central channel of the housing.

20 Claims, 6 Drawing Sheets

Related U.S. Application Data continuation of application No. 15/526,926, filed as application No. PCT/EP2015/079681 on Dec. 15, 2015, now Pat. No. 11,241,039.

(51) Int. Cl.
| | |
|---|---|
| *A24F 40/485* | (2020.01) |
| *A61M 11/04* | (2006.01) |
| *A61M 15/00* | (2006.01) |
| *A61M 15/06* | (2006.01) |
| *A24F 40/10* | (2020.01) |

(52) U.S. Cl.
CPC ........ *A61M 11/042* (2014.02); *A61M 15/008* (2014.02); *A61M 15/06* (2013.01); *A24F 40/10* (2020.01); *A61M 2205/3331* (2013.01); *A61M 2205/3653* (2013.01); *A61M 2205/8206* (2013.01)

(56) References Cited

U.S. PATENT DOCUMENTS

| | | |
|---|---|---|
| 9,603,389 B2 | 3/2017 | Chen |
| 9,648,905 B2 | 5/2017 | Levitz |
| 10,272,170 B2 | 4/2019 | Dubief |
| 10,543,323 B2 | 1/2020 | Buchberger |
| 10,750,784 B2 | 8/2020 | Mironov |
| 2005/0199236 A1 | 9/2005 | Fink |
| 2013/0087160 A1 | 4/2013 | Gherghe |
| 2014/0144429 A1 | 5/2014 | Wensley |
| 2014/0182610 A1 | 7/2014 | Liu |
| 2014/0305454 A1 | 10/2014 | Rinker |
| 2015/0090279 A1 | 4/2015 | Chen |
| 2015/0136156 A1 | 5/2015 | Liu |
| 2020/0275702 A1 | 9/2020 | Mironov |

FOREIGN PATENT DOCUMENTS

| | | |
|---|---|---|
| CN | 103237468 | 8/2013 |
| CN | 203243945 U | 10/2013 |
| CN | 103783674 | 5/2014 |
| CN | 103917119 | 7/2014 |
| CN | 103932401 | 7/2014 |
| CN | 103974637 | 8/2014 |
| CN | 104135881 A | 11/2014 |
| CN | 203986095 U | 12/2014 |
| CN | 203986096 U | 12/2014 |
| CN | 204070542 U | 1/2015 |
| CN | 204317492 U | 5/2015 |
| EP | 2 460 423 A1 | 6/2012 |
| JP | 2010-506594 A | 3/2010 |
| JP | 2012-506263 | 3/2012 |
| JP | 2013507152 | 3/2013 |
| KR | 10-0933516 | 12/2009 |
| WO | 00/09188 | 2/2000 |
| WO | 03/053502 | 7/2003 |
| WO | 2011/137453 A2 | 11/2011 |
| WO | 2013/083635 A1 | 6/2013 |
| WO | WO 2013/083638 A1 | 6/2013 |
| WO | 2013/159245 A1 | 10/2013 |
| WO | 2015/066127 A1 | 5/2015 |

OTHER PUBLICATIONS

Office Action issued in China for Application No. 201580060726.7 dated Nov. 1, 2019 (12 pages). English translation included.
PCT International Search Report and Written Opinion for PCT/EP2015/079681 dated Apr. 15, 2016 (11 pages).
PCT International Preliminary Report and Patentability for PCT/EP2015/079681 dated Apr. 13, 2017 (16 pages).
U.S. Office Action dated Dec. 16, 2020 in U.S. Appl. No. 16/877,464.
U.S. Appl. No. 16/877,464, filed May 18, 2020, 2020/0275695 A1, Eric Force, et al.
U.S. Appl. No. 15/526,926, filed May 15, 2017, 2017/0325505 A1, Eric Force, et al.
Japanese Office Action dated Nov. 17, 2021 in Japanese Application No. 2020-173132 (with Computer Generated English Translation).
Combined Office Action and Search Report dated Mar. 1, 2023 in the corresponding Chinese Patent Application No. 202010711926.7 (with English Translation and Translation of Category of Cited Documents), 37 pages.
Korean Office Action dated Jan. 17, 2023 in Korean Patent Application No. 10-2017-7012578 (with English language translation), 12 pages.

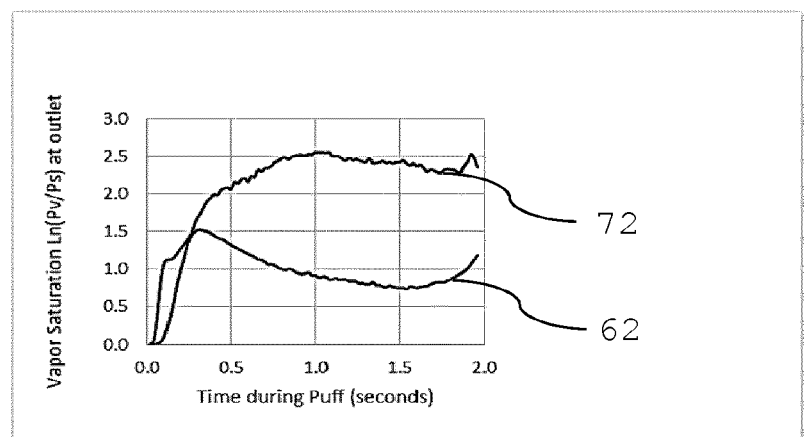
Fig. 6
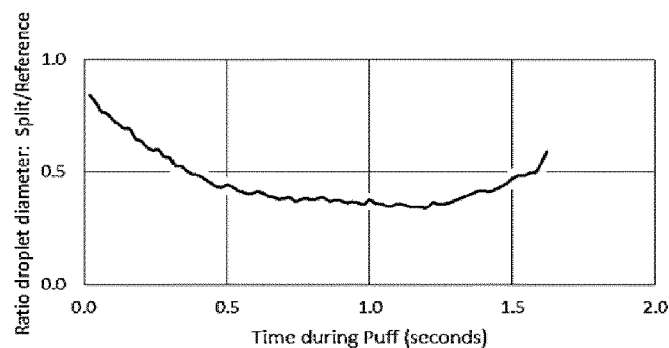
Fig. 7
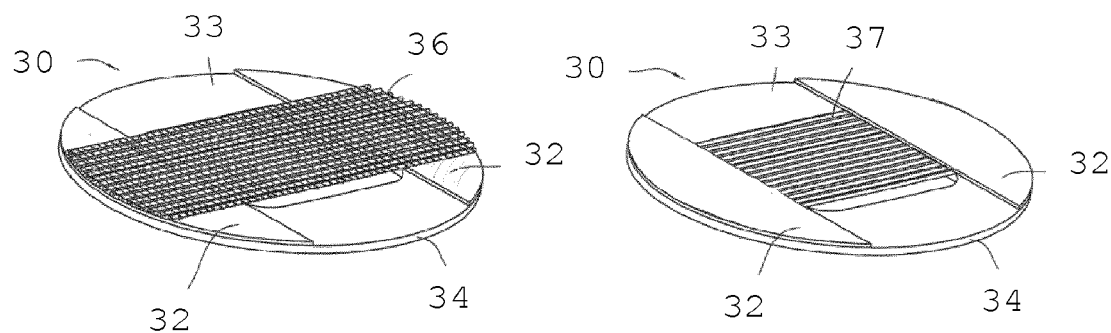
Fig. 8a
Fig. 8b

SPLIT AIRFLOW SYSTEM FOR AN ELECTRICALLY HEATED SMOKING SYSTEM AND METHOD FOR GUIDING AN AIRFLOW INSIDE AN ELECTRICALLY HEATED SMOKING SYSTEM

CROSS REFERENCE TO RELATED APPLICATIONS

This application is a continuation application of and claims the benefit of priority under 35 U.S.C. § 120 to U.S. application Ser. No. 16/877,464 filed on May 18, 2020, which is a continuation application of and claims the benefit of priority under 35 U.S.C. § 120 to U.S. application Ser. No. 15/526,926 filed on May 15, 2017, which is a National Stage Application of PCT/EP2015/079681, filed Dec. 15, 2015, and claims benefit of priority under 35 U.S.C. § 119 to European Patent Application No. 14197849.4, filed on Dec. 15, 2014, the entire contents of each of which are incorporated herein by reference.

The invention relates to electrically heated smoking systems and a method for guiding an airflow inside an airflow inside an electrically heated smoking system.

Some aerosol-generating systems such as electrically operated smoking devices may comprise a battery and control electronics, a cartridge comprising a supply of aerosol forming substrate and an electrically operated vaporizer. A substance is vaporized from the aerosol forming substrate, for example by a heater. An airflow is made to pass the heating element to entrain the vaporized liquid and guide it through a mouthpiece to a mouth end of the mouthpiece, while a user is puffing at the mouth end.

The airflow passing the heater may have a cooling action on the heater. This may lead to less vaporized liquid or may require more energy to keep the heater at a temperature sufficient for vaporizing an amount of liquid such as to achieve a desired amount of aerosol.

Thus, there is a need for electrically heated smoking systems and for a method for guiding an airflow inside electrically heated smoking system, which improve the efficiency of the electrically heated smoking system.

According to a first aspect, there is provided a split airflow system for an electrically heated smoking system for generating aerosol. The split airflow system has a downstream end and comprises a first channel defining a first flow route and a second channel defining a second flow route. The first channel and the second channel are at least partially distinct channels. The first flow route directs ambient air from outside the system to the downstream end of the system. The second flow route directs ambient air from outside the system towards a heating element, preferably a substantially flat, fluid permeable heating element, before conveying the ambient air to the downstream end. The first channel and the second channel define a total volume of ambient air passing through the system and the first channel provides at least 50 percent of the total volume of ambient air passing through the system.

Liquid vaporized by the heating element is collected by ambient air flowing in the second channel and is transported to the downstream end of the split airflow system. Ambient air is guided into the split airflow system and passes the heating element for taking up the liquid that has been vaporized by the heating element. This ambient air cools the heating element. The cooling effect is not only dependent on the temperature of the ambient air but also on the amount of ambient air coming into contact with the heating element. A first channel for directing ambient air along a first flow route not passing the heating element is now provided in the split airflow system according to the invention. The first channel also ends at the proximal end of the system, preferably at a mouth end of a mouthpiece of an electrically operated smoking system. However, ambient air entering the split airflow system is split along the first flow route and the second flow route in the first channel and the second channel, respectively. Preferably, the first channel bypasses at least those portions of the second channel that are arranged upstream of the position of the heating element. By this, only a portion of the total volume of ambient air entering the system passes the heating element. Another portion of the total volume of ambient air is directly, that is without passing the heating element, guided to the downstream end of the split airflow system.

By this measure, a variable volume of ambient air may be bypassing the heating element. The ambient air that passes the heating element and that may have a cooling effect on the heating element may be varied and may be controlled. Since only half or preferably less than half of the total volume of ambient air passes the heating element, the heating element is not cooled as much as if the total volume of ambient air would be passing the heating element. Thus, the heating element may be operated at lower energy. This saves energy and may lead to a battery of a smoking system comprising the split airflow system to have longer operating hours or may lead to a downsizing of such a battery. In addition, if a heating element may be operated at lower energies, the risk of a malfunctioning of the heating element, for example due to electrical short-cuts, or high temperature spikes, may be reduced or omitted.

Yet further, since the ambient air in the first channel has not passed the heating element, this ambient air is cooler than the aerosol carrying ambient air in the second channel. Thus, the ambient air in the first channel may have a cooling effect on the aerosol carrying ambient air. This effect is in particular pronounced, if the first flow route is joined with the second flow route before reaching the downstream end of the system. Then the first airflow is mixed with the second airflow inside, for example, inside a mouthpiece and is cooled more rapidly. This may result in oversaturation of the air with the vaporized liquid. This again may result in the formation of smaller aerosol droplets.

Preferably, the first channel provides between about 50 percent and about 95 percent of the total volume of ambient air passing through the split airflow system. More preferably, the first channel provides between about 65 percent and about 95 percent of the total volume of ambient air passing through the split airflow system, even more preferably, between about 85 percent and about percent.

It has been found that a small airflow passing the heating element suffices to entrain the vaporized liquid and guide it to a downstream end of the system. The smaller the ambient airflow passing the heating element, the less heat loss due to cooling of the heating element by the passing airflow. The above flow volumes of the second channel have shown to entrain vaporized liquid particularly well and by an at the same time low cooling of the heating element. Preferably, the mentioned percent of volume of the total volume of ambient air are applied in an aerosol generating smoking system preferably comprising a substantially flat heating element, more preferably a substantially flat, fluid permeable heating element, for example a heating element comprising a plurality of electrically conductive filaments such as a mesh heating element.

The volume of the ambient air passing through the second channel and passing the heating element may be varied and adapted to, for example, the kind of heating element applied or the amount of vaporized liquid available. For example, the volume of ambient air passing the heating element may be adapted to a total area, which is effectively heated by the heating element.

As a general rule, whenever the term 'about' is used in connection with a particular value throughout this application this is to be understood such that the value following the term 'about' does not have to be exactly the particular value due to technical considerations. However, the term 'about' used in connection with a particular value is always to be understood to include and also to explicitly disclose the particular value following the term 'about'.

The terms 'upstream' and 'downstream' are used herein in view of the direction of an airflow in the system. Upstream and downstream ends of the system are defined with respect to the airflow when a user draws on the proximal or mouth end of the aerosol-generating smoking article. Air is drawn into the system at an upstream end, passes downstream through the system and exits the system at the proximal or downstream end. The terms 'proximal' and 'distal' as used herein refer to the position of an element with respect to its orientation to a consumer or away from a consumer. Thus, a proximal end of a mouthpiece of aerosol-generating system corresponds to the mouth end of the mouth piece. A distal opening of a cartridge housing corresponds to a position of an opening arranged in the cartridge housing facing away from a consumer, accordingly.

The term 'substantially flat' heating element is used throughout the specification to refer to a heating element that is in the form of a substantially two dimensional topological manifold. Thus, the substantially flat heating element extends in two dimensions along a surface substantially more than in a third dimension. In particular, the dimensions of the substantially flat heating element in the two dimensions within the surface is at least 5 times larger than in the third dimension, normal to the surface. An example of a substantially flat heating element is a surfaces, wherein the distance between these two imaginary surfaces is substantially smaller than the extension within the surfaces. In some preferred embodiments, the substantially flat heating element is planar. In other embodiments, the substantially flat heating element is curved along one or more dimensions, for example forming a dome shape or bridge shape. A flat heating element can be easily handled during manufacture and provides for a robust construction.

Heating elements as used in the split airflow system or in the smoking system may for example be wick-coil heaters as known on the art. Therein, a coil is wound around a wick, which wick is immersed into a liquid to be vaporized. The liquid is transported by capillary action outside of its cartridge to the portion of the wick where the coil is wound around the wick and heating this wick portion.

Preferably, fluid permeable heating elements are used. Fluid permeable heating elements are suitable for vaporizing liquids of different kind of cartridges. For example, as a liquid aerosol-forming substrate, a cartridge may contain a liquid or a liquid containing transport material such as for example a capillary material. Such a transport material and capillary material actively conveys liquid and is preferably oriented in the cartridge to convey liquid to the heating element. A filament arrangement of the heating element is arranged close to the liquid or to the liquid containing capillary material such that heat produced by a heating element may vaporize the liquid. Preferably, filament arrangement and aerosol-forming substrate are arranged such that liquid may flow into interstices of the filament arrangement by capillary action. The filament arrangement may also be in physical contact with a capillary material.

Preferably, a fluid permeable heating element is a substantially flat heating element. Such a heating element may for example be a flat coil embedded in a porous ceramic or a mesh heater, wherein a mesh or another filament arrangement is arranged over an opening in the heater. The heating element may for example comprise an electrically conductive mesh or coil pattern printed onto a heat resistance support piece. The support piece may for example be ceramic, polyether ether ketone (PEEK), or other thermally resistant ceramics and polymers that do not thermally decompose and release volatile elements at temperatures below 200 C and preferably at temperatures below 150 C.

The term 'filament' is used throughout the specification to refer to an electrical path arranged between two electrical contacts. A filament may arbitrarily branch off and diverge into several paths or filaments, respectively, or may converge from several electrical paths into one path. A filament may have a round, square, flat or any other form of cross-section. A filament may be arranged in a straight or curved manner.

The term 'filament arrangement' is used throughout the specification to refer to an arrangement of one or preferably a plurality of filaments. The filament arrangement may be an array of filaments, for example arranged parallel to each other. Preferably, the filaments may form a mesh. The mesh may be woven or non-woven. Preferably, the filament arrangement has a thickness of between about 0.5 micrometers and 500 micrometers. The filament arrangement may, for example, be in the form of an array of parallel or crosswise electrically conductive filaments. The filament may be integrally formed with electrical contacts, for example formed from an electrically conductive foil, for example, stainless steel foil, that is etched to define the filaments.

The heating element vaporizes liquid from a cartridge or cartridge housing comprising an aerosol-forming substrate. The aerosol-forming substrate is a substrate capable of releasing volatile compounds that can form an aerosol. The volatile compounds may be released by heating the aerosol-forming substrate.

The aerosol-forming substrate may comprise plant-based material. The aerosol-forming substrate may comprise tobacco. The aerosol-forming substrate may comprise a tobacco-containing material containing volatile tobacco flavour compounds, which are released from the aerosol-forming substrate upon heating. The aerosol-forming substrate may alternatively comprise a non-tobacco-containing material. The aerosol-forming substrate may comprise homogenised plant-based material. The aerosol-forming substrate may comprise homogenised tobacco material. The aerosol-forming substrate may comprise at least one aerosol-former. An aerosol-former is any suitable known compound or mixture of compounds that, in use, facilitates formation of a dense and stable aerosol and that is substantially resistant to thermal degradation at the operating temperature of operation of the system. Suitable aerosol-formers are well known in the art and include, but are not limited to: polyhydric alcohols, such as triethylene glycol, 3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. Preferred aerosol formers are polyhydric alcohols or mixtures thereof, such as triethylene glycol, 1,3-butanediol and, most preferred, glycerine. The aerosol-forming substrate may comprise other additives and ingredients, such as flavourants.

The aerosol forming substrate may be conveyed to the heating element via a capillary material in contact with or adjacent to the heating element. The capillary material may have a fibrous or spongy structure. The capillary material preferably comprises a bundle of capillaries. For example, the capillary material may comprise a plurality of fibres or threads or other fine bore tubes. The fibres or threads may be generally aligned to convey liquid to the heating element. Alternatively, the capillary material may comprise sponge-like or foam-like material. The structure of the capillary material forms a plurality of small bores or tubes, through which the liquid can be transported by capillary action. The capillary material may comprise any suitable material or combination of materials. Examples of suitable materials are a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres or ceramic. The capillary material may have any suitable capillarity and porosity so as to be used with different liquid physical properties. The liquid has physical properties, including but not limited to viscosity, surface tension, density, thermal conductivity, boiling point and vapour pressure, which allow the liquid to be transported through the capillary device by capillary action.

The capillary material may be in contact with electrically conductive filaments of the heating element. The capillary material may extend into interstices between the filaments. The heating element may draw liquid aerosol-forming substrate into the interstices by capillary action. The capillary material may be in contact with the electrically conductive filaments over substantially the entire extent of an aperture in the heating element.

The heating element may be provided in a heating assembly including support elements. The heating assembly may contain two or more different capillary materials, wherein a first capillary material, in contact with the heating element, has a higher thermal decomposition temperature and a second capillary material, in contact with the first capillary material but not in contact with the heating element has a lower thermal decomposition temperature. The first capillary material effectively acts as a spacer separating the heating element from the second capillary material so that the second capillary material is not exposed to temperatures above its thermal decomposition temperature. As used herein, 'thermal decomposition temperature' means the temperature at which a material begins to decompose and lose mass by generation of gaseous by products. The second capillary material may advantageously occupy a greater volume than the first capillary material and may hold more aerosol-forming substrate that the first capillary material. The second capillary material may have superior wicking performance to the first capillary material. The second capillary material may be a less expensive or have a higher filling capability than the first capillary material. The second capillary material may be polypropylene.

According to an aspect of the split airflow system according to the invention, the first channel converges with an end portion of the second channel such that the first flow route joins the second flow route after the second flow route has directed ambient air past the heating element, that is the first flow route joins the second flow route downstream of the heating element.

In such embodiments ambient air may leave the downstream end of the split airflow system or for example a mouthpiece of a smoking system at one or several common outlet openings. Preferably, a most downstream portion of the second channel is identical with the first channel. This may simplify a manufacturing of a smoking system. For example, in a mouthpiece a single additional bore may be provided in the mouthpiece wall to extend into the mouthpiece to the second channel to form the first channel. By this, also existing mouthpieces may be adapted to a split airflow system without having to reconstruct the entire mouthpiece. The aerosol containing ambient air is mixed with 'fresh' ambient air guided into the system by the first flow route. Thereby, the aerosol containing ambient air is cooled. The cool air supports the formation of smaller aerosol droplet sizes compared to the same air at higher temperatures. Cool air seems to support supersaturation of the air with vaporized liquid. Supersaturation has an effect on the sizes of droplets formed in the supersaturated air.

According to an alternative aspect of the split airflow system according to the invention, the first channel and the second channel form distinct channels such that the first flow route and the second flow route direct ambient air from outside the system to the downstream end of the system separate from each other. Thus, ambient air is drawn into the split airflow system, guided in and though the system and out of the system along entirely separate flow routes. By this, ambient air passing the heating element and ambient air bypassing the heating element do not compete or influence each ether. Having a separate first channel provides many constructional possibilities to guide ambient air though the system or through a mouthpiece independent of the aerosol carrying ambient air in the second channel.

According to another aspect of the split airflow system according to the invention, at least a portion of the second channel and the heating element are arranged perpendicular to each other such that the at least a portion of the second channel directs ambient air to impinge perpendicular onto the heating element.

Letting ambient air to impinge onto the heating element is an efficient way to direct ambient air to the heating element and carry aerosol away from the heating element. In particular, if the ambient air impinges onto the center of a heating element, a homogeneous airflow over the heating element may be provided in a radially outward direction. The ambient air may impinge onto the center only of the heating element.

In the split airflow system according to the invention, at least a portion of the second channel arranged downstream of the heating element, may be arranged in the circumference of the heating element, preferably in the circumference only. Preferably, a plurality of second channel portions is arranged in the circumference of the heating element. By this the vapour containing ambient air is guided away from the heating element at the circumference of the heating element, for example in longitudinal direction along the circumference of, for example, a housing or a mouthpiece of an electrically heated smoking system. The large area such vapour containing ambient air is guided along, as well as the closeness to an environment may both support a cooling of the vapour containing air and support aerosol formation. If at least a channel portion of a first channel is arranged parallel to the at least one portion of the circumferentially arranged second channel arranged downstream of the heating element, additional cooling may be provided through fresh ambient air flowing through the first channel portion and thermal contact between the respective first channel portions and second channel portions. Preferably, a plurality of first channel portions is arranged in longitudinal direction along the circumference of a mouthpiece. An arrangement of channel portions in a circumference only, leaves options of having other channels arranged in, for example, of a center only or having radially arranged channel portions connecting central and circumferential channel portions or central channel portions with the environment.

The first flow route and the second flow route may be selected to achieve a desired result, for example a predefined airflow splitting with predefined air volumes passing through the respective channels. For example, a length or diameter of a channel may be varied, for example also to achieve a predefined resistance to draw (RTD). First and second flow route are also selected accordinc to a set-up of an aerosol generating smoking system and the arrangement and characteristics of the individual components of the smoking system. For example, aerosol may be generated at a proximal end or at a distal end of a cartridge housing containing the aerosol-forming substrate. Depending on the orientation of the cartridge in the aerosol-generating smoking system, the open end of the cartridge housing is arranged to face a mouthpiece or is arranged facing away from the mouthpiece. Accordingly, a heating element for heating the aerosol-forming substrate is arranged at a proximal or distal end of the housing. Preferably, liquid is vaporized at the open distal end of the mouthpiece and a heating element is arranged between cartridge and mouthpiece.

Preferably, a first flow route and first channel, accordingly, are entirely arranged in a mouthpiece of the smoking system. Preferably, a first air inlet is then arranged in a side wall of the mouthpiece, while the one or several outlets of the first channel are arranged in the proximal or mouth end of the mouthpiece. A second flow route is dependent on the location of the heating element in the smoking system. For example, if a heating element is arranged at an open proximal end of the cartridge housing, for example to cover the proximal end of the cartridge (top version), the second channel may also be arranged entirely in a mouthpiece.

The first channel and the second channel may diverge into several channel portions and several channel portions of a first channel or of a second channel may converge into a single first channel or second channel, respectively. In addition, a first channel may consist of several first partial channels and a second channel may consist of several second partial channels. There, a sum of first partial channels provide for the volume of ambient air of the first channel and a sum of second partial channels provide for the volume of ambient air of the second channel. The total number of air inlets for both the first and second partial channels may preferably be between 2-10, more preferably between 6-10, and most preferably between 8-10. For example, a sum of first partial channels that provide for the volume of ambient air of the first channel may have 7 or 9 inlets in fluid communication with the first channel and a sum of second partial channels provide for the volume of ambient air of the second channel via 1 or 2 inlets in fluid communication with the second channel.

In embodiments where a heating element is arranged at an open distal end of a cartridge housing, for example to cover the open distal end of the cartridge (bottom version), the second flow route routinely starts at a further distal location in the smoking system, for example in the region of a distal end of the cartridge housing. A second air inlet of the second channel may for example be arranged in a main housing of the system. Ambient air is then directed into the system, passes the heating element at the distal end of the cartridge and entrains vapour generated by heating the aerosol-forming substrate in the cartridge. The aerosol containing air may then be guided along the cartridge between a cartridge housing and a main housing to the downstream end of the system, where it is mixed with ambient air from the first flow route (either before or upon reaching the downstream end).

An inlet opening of the second channel arranged in a region of a distal end of a cartridge housing may also be provided in a top version, that is in embodiments, where a heating element is arranged at a proximal end of the cartridge. The second flow route may not only pass outside of the cartridge but also through the cartridge. Ambient air then enters the cartridge at a semi-open wall of the cartridge, passes through the cartridge and leaves the cartridge by passing though the heating element arranged at the proximal end of the cartridge. Thereby, ambient air may pass through the aerosol-forming substrate or through one or several channels arranged in a solid aerosol-forming substrate such that ambient air does not pass through the substrate itself but in the channels next to the substrate.

For allowing ambient air to enter a cartridge, a side wall of the cartridge housing, preferably a wall opposite the heating element, preferably a bottom wall, is provided with at least one semi-open inlet. The semi-open inlet allows air to enter the cartridge but no air or liquid to leave the cartridge through the semi-open inlet.

A semi-open inlet may for example be a semi-permeable membrane, permeable in one direction only for air but is air- and liquid-tight in the opposite direction. A semi-open inlet may for example also be a one-way valve. Preferably the semi-open inlets allow air to pass through the inlet only if specific conditions are met, for example a minimum depression in the cartridge or a volume of air passing through the valve or membrane.

Such one-way valves may, for example, be commercially available valves, such as for example used in medical devices, for example LMS Mediflow One-Way, LMS Sure-Flow One-Way or LMS Check Valves (crosses membranes). Suitable membranes to be used for a cartridge having an airflow passing through the cartridge, are for example vented membranes as used in medical devices, for example Qosina Ref. 11066, vented cap with hydrophobic filter or valves as used in baby bottles.

Such valves and membranes may be made of any material suitable for applications in electrically heated smoking systems. Materials suitable for medical devices and FDA approved materials may be used; for example Graphene having very high mechanical resistance and thermal stability within a large range of temperatures. Preferably, valves are made of soft resilient material for supporting a liquid-tight incorporation of the one or several valves into a wall of the cartridge housing.

Letting ambient air pass through the substrate supports an aerosolization of the aerosol-forming substrate. During puffing, a depression occurs in the cartridge, which may activate the semi-open inlets. Ambient air then passes the cartridge, preferably a high retention or high release material (HRM) or a liquid, and crosses the heating element, thereby creating and sustaining aerosolization of the liquid, when the heating element sufficiently heats the liquid. In addition, due to the depression caused during puffing, a supply of liquid in a transport material such as a capillary material to the heating element may be limited. An ambient airflow through the cartridge may equalize pressure differences within the cartridge and thereby support an unhindered capillary action towards the heating element.

A semi-open inlet may, in addition, or alternatively also be provided in one or several side walls of the cartridge housing. Semi-open inlets in side walls provide a lateral airflow into the cartridge towards the open top end of the cartridge housing, where the heating element is arranged. Preferably, lateral airflows pass through the aerosol-forming substrate.

If an air inlet of a second channel is arranged in a mouthpiece, a way from the inlet to the heating element may be kept short thus possibly reducing a resistance to draw. Air may also be guided in radial direction from one side of the heating element to the other side or, for example, from a peripheral side of the heating element to the center of the heating element.

The second flow route may provide many variants to supply ambient air to the heating element and transport aerosol away from the heating element and to a downstream end of the system. For example, a radial supply of ambient air is preferably combined with and large central extraction. A central supply of ambient air is preferably combined with a radial distribution of the air over an entire heating element surface with a circumferential conveying of the aerosol containing air to the downstream end. The second flow route may direct ambient air to impinge onto the heating element, for example perpendicular to the heating element, preferably onto a center of the heating element.

Airflow directed perpendicularly or parallel to a center portion of heating element demonstrates improved aerosolization in terms of smaller particle sizes and higher amounts of total particulate matter present in the aerosol stream when compared to airflow that impinges the surface at an angle greater than 0 and less than 90 degrees. This may be due to a lower level of turbulences created at the heater element and airflow interface, improved aerosol production by maximizing the whole of the heater (for example, portions outside of the center portion of the heater element contribute additional or higher amounts of aerosol), or due to a higher wicking effect based on a higher volume of air crossing the heating element.

According to another aspect of the invention, there is provided a method for guiding an airflow in an electrically heated smoking system for generating aerosol. The method comprises the steps of directing ambient air from outside the system to a downstream end of the system along a first flow route and directing ambient air from outside the system towards a heating element, preferably a substantially flat, fluid permeable heating element, before conveying the ambient air to the downstream end of the system along a second flow route. Therein, a total volume of ambient air passes through the system along the first flow route and along the second flow route, and at least 50 percent of the total volume of ambient air through the system passes along the first flow route.

According to an aspect of the method according to the invention, the method further comprises the step of joining ambient air of the first flow route and ambient air of the second flow route before the ambient air of the first flow route and of the second flow route reach the downstream end of the system.

According to another aspect of the method according to the invention, the method further comprises the step of keeping the first flow route separate from the second flow route.

According to yet another aspect of the method according to the invention, the method comprises the step of directing the ambient air in the second flow route such that the ambient air in the second flow route impinges substantially perpendicularly onto the heating element.

Further aspects and advantages of the method according to the invention are mentioned relating to the split airflow system and smoking system according to the invention and will not be repeated.

According to a further aspect of the method according to the invention, the method further comprises the steps of providing a liquid aerosol forming substrate, heating the heating element, thereby vaporizing liquid from the aerosol forming substrate and forming aerosol and letting the ambient air directed to the heating element by the second flow route pick up the formed aerosol before conveying the aerosol containing ambient air to the downstream end of the system.

According to another aspect of the method according to the invention, the method further comprises the steps of providing at least a portion of the first channel and at least a portion of the second channel inside a mouthpiece of the system, wherein the downstream end of the system is a proximal end of the mouthpiece. The method further comprises the steps of guiding ambient air in the at least a portion of the second channel along a length of the mouthpiece in a direction towards the proximal end of the mouthpiece, performing an inversion of direction of the ambient air in the second channel, and guiding the ambient air in the direction of the heating element for impinging the ambient air onto the heating element.

According to some embodiments of the method according to the invention, the ambient air is guided in the at least a portion of the second channel along a central axis of the mouthpiece, and is made to impinge substantially centrally onto the heating element.

The method may further comprise the steps of guiding aerosol containing ambient air from a center of the heating element, where the ambient air preferably impinged perpendicularly onto the heating element, radially outwardly to the circumference of the heating element and circumferentially downstream into the direction of an outlet opening. The step of guiding the aerosol containing ambient air circumferentially downstream may, for example, be performed in a plurality of circumferentially arranged channel portions.

The method may comprise the step of arranging a substantially flat fluid permeable heating element in the electrically heated smoking system. Preferably, the heating element is arranged in a manner to face an open distal end of the mouthpiece of the smoking system. Preferably, the fluid permeable heating element comprises a plurality of electrically conductive filaments. A plurality of filament, for example an array of parallel arranged filaments or a mesh, provide a good vaporization of liquid and a good permeability of vaporized liquid through interstices between the filaments. Such filaments or mesh heating elements are inexpensive to produce and robust, especially compared to coil and wick heaters. Mesh heating elements may be manufactured in a substantially flat manner, which is space saving. Mesh heating elements are also easy to handle, especially upon mounting of the heating element or cartridge comprising the heating element.

According to yet another aspect of the invention, there is also provided an electrically heated smoking system for generating aerosol comprising the split airflow system as described herein. The smoking system comprises a storage portion comprising a housing for holding a liquid aerosol-forming substrate, the housing having an open end. The smoking system also comprises a heating element, preferably a substantially flat, fluid permeable heating element, extending over the open end of the housing and a mouthpiece arranged adjacent the housing. The mouthpiece comprises an elongate body comprising an open distal end, the open distal end facing the housing. The mouthpiece further comprises a first channel arranged in the mouthpiece, wherein the first channel comprises a first inlet opening arranged in a side wall of the elongate body and an outlet opening arranged at a proximal end of the elongate body for defining a first flow route directing ambient air from outside the system through the mouthpiece to the outlet opening. The mouthpiece also comprises an end portion of a second channel extending between the open distal end of the elongate body and the proximal end of the elongate body. The second channel is arranged in the smoking system and defines a second flow route. The second flow route directs ambient air entering the smoking system to the heating element, where the ambient air is capable of entraining aerosol generated by vaporizing liquid through heating the heating element, before conveying the aerosol containing ambient air to the proximal end of the elongate body of the mouthpiece. The first channel and the second channel define a total volume of ambient air passing through the smoking system and the first channel provides at least 50 percent of the total volume of ambient air passing through the smoking system. Ambient air from outside the system is split to pass along a first flow route in the first channel and to pass along a second route in the second channel.

Preferably, the heating element is arranged between the mouthpiece and the aerosol generating substrate.

According to an aspect of the smoking system according to the invention, the first channel converges with the end portion of the second channel downstream of the open distal end of the elongate body. By this, the ambient air of the first channel does not pass the heating element. A first inlet opening of the first channel is fluidly connected to an outlet opening at the downstream end of the system, that is, in the proximal end of the mouthpiece.

According to another aspect of the smoking system according to the invention, the second channel comprises a second outlet opening arranged at the proximal end of the elongate body. The second outlet opening is separate from the outlet opening of the first channel.

According to a further aspect of the smoking system according to the invention, a second inlet opening of the second channel is arranged in the side wall of the elongate body.

In the smoking system according to the invention, the second channel may comprise at least one second channel portion arranged downstream of the heating element carrying the aerosol containing ambient air. The at least one second channel portion is arranged in longitudinal direction along the circumference of the housing or of the mouthpiece.

Aspects and advantages of the electrically heated smoking system have been described relating to the split airflow system and method for guiding an airflow in an electrically heated smoking system and will not be repeated.

According to some embodiments of the smoking system according to the invention an upstream portion of the second channel is arranged parallel to a side wall of the elongate body of the mouthpiece or of the housing before an intermediate portion of the second channel directs in a radial direction of the elongate body. Such a flow route may for example be used to direct the ambient air to be guided essentially parallel to portions of the ambient air already carrying aerosol. By this, an additional cooling of the aerosol by the ambient air may be achieved.

According to another aspect of the smoking system according to the invention, the heating element is a fluid permeable heating element comprising a plurality of electrically conductive filaments.

According to a further aspect of the smoking system according to the invention, the second channel comprises a plurality of second channel end portions arranged in longitudinal direction along the circumference of the elongate body. Preferably, ambient air is guided to the center of the heating element. A homogeneous extraction of aerosol from the heating element with the ambient air may be provided: the centrally impinging ambient air may flow radially outwardly on the surface of the heating element. In addition, the aerosol containing ambient air may be cooled on a large total surface area, which may further support formation of small-sized aerosol particles.

The invention is further described with regard to embodiments, which are illustrated by means of the following drawings, wherein:

FIG. 6 shows average vapour saturation curves at the outlet of the mouthpiece;

FIG. 7 shows the ratio of droplet diameters at the outlet of the mouthpiece for total and split airflow geometries;

FIGS. 8a to 8f shows heating elements as may be used in the smoking system according to the invention;

Figure 1:
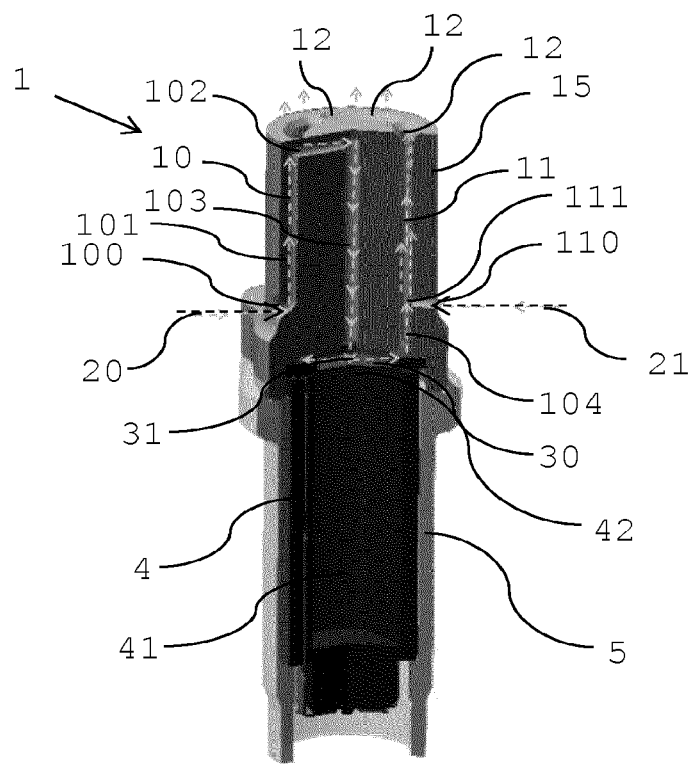
FIG. 1 shows an embodiment of the split airflow system.

In FIG. 1 a cartridge 4 and mouthpiece 1 embodiment for an aerosol generating smoking system is shown. An elongate main housing 5 accommodates a cartridge with a tubular shaped cartridge housing 4 containing an aerosol-forming substrate, for example a liquid containing capillary material 41. The cartridge housing has an open proximal end 42. A heater 30, preferably, a substantially flat mesh heater, is arranged to cover the open proximal end of the cartridge housing 4. The heating element may or may not be in direct physical contact with the aerosol-forming substrate 41. A mouthpiece 1 having a substantially tubular shaped elongate body 15 is aligned with the main housing, the cartridge housing 4 and the heating element 30. The elongate body 15 has an open distal end facing the heater 30.

The embodiment shown in FIG. 1 comprises a second channel 10 defining a second flow route in the mouthpiece 1 leading incoming second ambient air 20 over the heater 30 and to air outlets 12 at a proximal end or mouth end of the mouthpiece 1, where a consumer puffs. Also a first channel 11 defining a first flow route is arranged in the mouthpiece 1. First ambient air 21 enters the first channel 11 through a first inlet 110 and is directly led to the cutlets 12 without passing the heater 30. This first airflow 21 joins the second airflow 20 in the second channel 10 at a location 111 downstream of the heater 30 and upstream of the outlets 12. A most downstream portion of the second channel 10 is identical with the first channel 11. The second airflow 20 passes the heater 30, where aerosol formed by heating the heater and vaporizing liquid from the aerosol-forming substrate 41, and entrains the aerosol in the second airflow 21. The aerosol carrying second airflow is combined with the first airflow 21 at location 111. The first airflow 21 mixes with the aerosol carrying second airflow and cools it.

Second inlet 100 and first inlet 110 are both openings or bore holes in the mouthpiece 1 in a distal half of the elongate body 15 of the mouthpiece 1. The second flow route in an upstream second channel portion 101 runs in the elongate body parallel to the circumference of the elongate body to the proximal end of the mouthpiece. In a radially inwardly directing portion 102 of the second channel 10, the second airflow 20 is directed to the center of the elongate body and in a centrally arranged portion 103 of the second channel the second airflow 20 is directed to the heater 30 to impinge to the center 31 of the heater 30. The second airflow 20 passes over the heater 30 and spreads radially outwardly to several longitudinal end portions 104 of the second channel 10. The longitudinal end portions 104 are regularly arranged along the circumference within the elongate body.

In this embodiment a first flow route and a second flow route and a first channel and a second channel, respectively, are arranged entirely within the mouthpiece 1 of the aerosol generating system.

Figure 2:
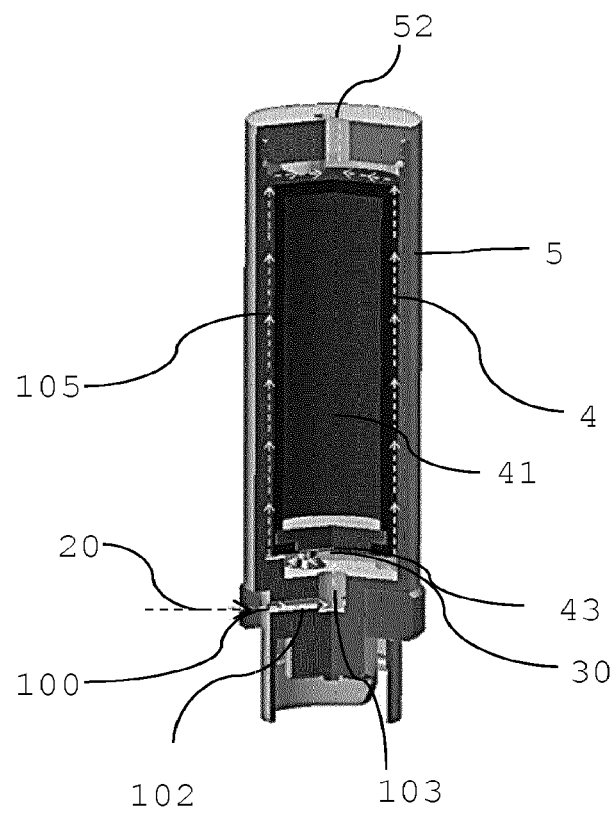
FIG. 2 shows another embodiment of a second flow route in the split airflow system.

In FIG. 2 an embodiment of a cartridge 4 with heater 30 arranged at the bottom of the cartridge covering an open distal end 43 of the cartridge housing 41 is illustrated. A second inlet 100 is arranged in the main housing 5 and the ambient air is directly led in a radially inwardly directing portion 102 of the second channel to the center of the main housing. In a centrally arranged portion 103 of the second channel, the air is directed to impinge perpendicularly onto the heater 30. The air then passes the heater 30, entrains aerosol caused by heating the liquid in the aerosol-forming substrate 40 through the heater 30. The aerosol containing air is led to the proximal end of the cartridge 4 in several longitudinal portions 105 of the second channel 10 arranged between and along cartridge housing 41 and main housing 5. There, the aerosol containing second airflow is guided to and out of a single centrally arranged opening 52 in the main housing 5. A mouthpiece (not shown) may be arranged adjacent the main housing. Preferably, the mouthpiece then also has a centrally arranged opening and end portion 104 of second channel 10 to receive the aerosol containing second airflow and guide it to a single outlet opening 12 in the proximal end of the mouthpiece 1. In such an embodiment, a first channel 11 may basically be similar to the embodiment shown in FIG. 1. The first channel may be a separate channel in the mouthpiece or may comprise a radial bore that extends to the second channel in the mouthpiece such that the first airflow may be joined with the second airflow within the mouthpiece.

Figure 3:
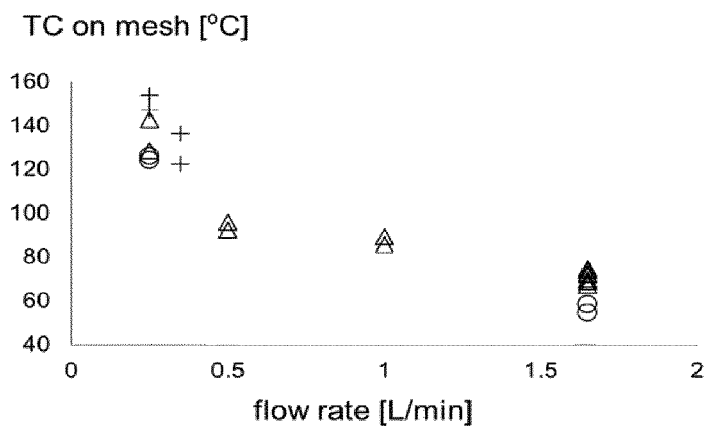
FIG. 3 shows the cooling effect of different airflows on different heating element.

The data shown in FIG. 3 demonstrate the effect of cooling a mesh heater the more the higher a flow rate of air passing the mesh heater. Cooling rates were measured using different mesh heaters: Reking (45 micrometers/180 per inch), Haver (25 micrometers/200 per inch) and 3 strips Warrington (25 micrometers/250 per inch). Measurement data for the Reking heater are indicated by crosses, measurement data for the Haver heater are indicated by circles and measurement data for the 3 strips Warrington heater are indicated by triangles. All heaters were operated at three Watt. Temperature was measured with a thermocouple coupled to the heaters. Increasing the flow rate as indicated on the x-axis in liter per minute [L/min] results in a lower measured temperature on the mesh heater. Typical sizes of airflows in aerosol-generating systems can be approximated by standard smoking regimes, for example the Health Canada smoking regime, which leads to significant cooling of the heater. Exemplary smoking regimes such as Health Canada draw 55 ml of a mix of air and vapour over 2 seconds. An alternative regime is 55 ml over 3 seconds. Neither exemplary smoking regime mimics behaviour precisely but instead acts as a proxy to what an average user would draw.

Experiments with split airflow systems were preferably made with the first airflow having between 6/7 and 8/9 of the total volume of ambient air. The volume of ambient air directed to the heater had a volume between 1/7 and 1/9 of the total volume of ambient air, accordingly. About 85 percent to 89 percent of the total volume of ambient air is thus directly conveyed through the outlet of the mouthpiece, while only about 11 percent to about 15 percent of the total volume of airflow pass the heater.

Exemplary values for the channels as for example shown in the embodiment of FIG. 1, are:

Air inlet of the second channel: diameter 0.75 millimeter and total channel cross section 0.44 square millimeter.

Air inlet of first channel: diameter 1 millimeter times 4 and 3.14 square millimeter total channel cross section.

Figure 4:
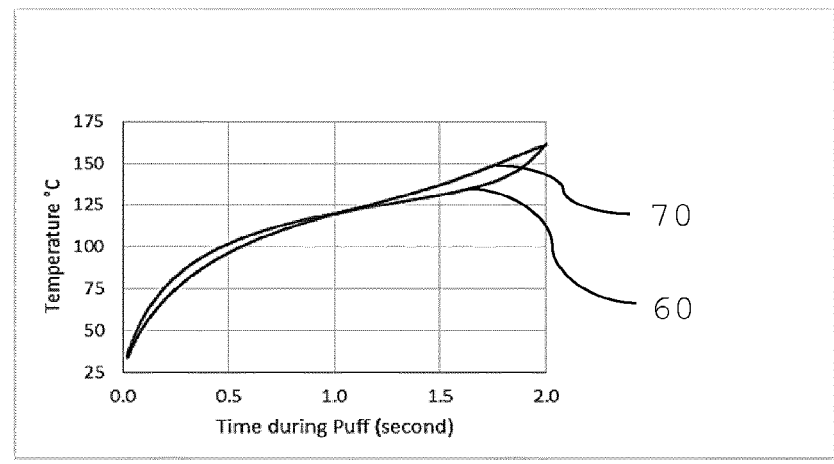
FIG. 4 shows temperature curves of differently powered heating elements.

In the graph of FIG. 4, average temperatures at the heater versus time during one puff is shown. Curve 60 represents reference temperature data for the heater, where the total airflow is directed to the heater. Curve 70 represents temperature data for the heater in a split airflow system, where only one/seventh of the total airflow is directed to the heater. For the reference data the heater had been heated with 5 Watt, while the heater receiving a reduced airflow had been heated with 4 Watt. It can be seen that with a split airflow, energy of 1 Watt during the length of one puff may be saved.

Figure 5:
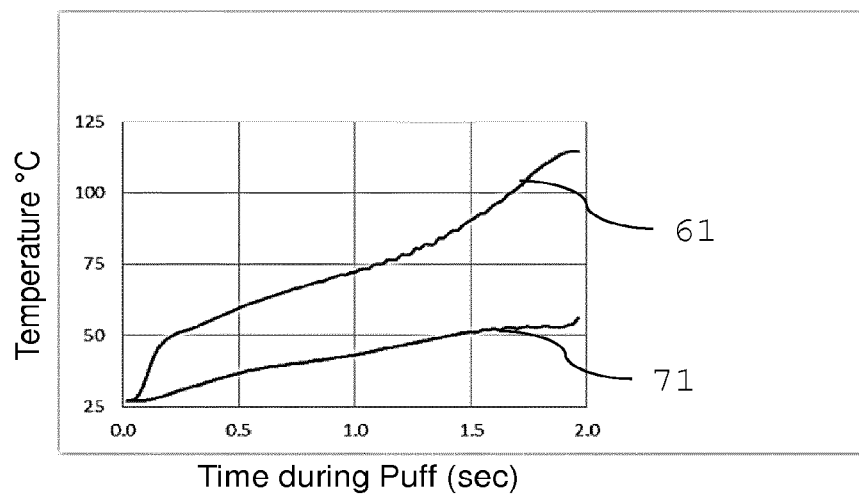
FIG. 5 shows temperature curves at the outlet of the mouthpiece.

FIG. 5 shows the effect of the split airflow onto the temperature of the aerosol carrying airflow at the outlet of the mouthpiece during one puff. These data refer to embodiments of mouthpieces, where the first airflow joins the aerosol carrying second airflow within the mouthpiece, as shown in FIG. 1. Temperature curve 61 represents outlet air temperatures for a heater powered with 5 Watt with the total airflow impinging on the heater. Temperature curve 71 represents outlet air temperatures for a heater powered with 4 Watt, where one/seventh of the total airflow only is directed to the heater. There are significant lower temperatures of the aerosol carrying airflow at the outlet of the mouthpiece due to the six/seventh volume of 'fresh' air joining the aerosol stream. Typically 'fresh' air mixed into the aerosol carrying airflow is at room temperature.

Significant difference may also be seen in the ratio of vapour pressure to the saturation pressure (Pvapor/Psaturation) of a glycerol solution at the outlet of the mouthpiece during one puff. This ratio is shown in FIG. 6. Curve 72 refers to pressure data at the outlet for the heater powered with 4 Watt, in the split airflow system with one/seventh of the total airflow directed to the heater. Curve 62 refers to pressure data at the outlet for the heater powered with 5 Watt with the total airflow impinging on the heater. The pressure ratio is higher for the split airflow embodiment due to the cooling effect. This represents a larger degree of super saturation of the glycerol solution, which favours aerosolization with smaller droplets. Simulation clearly predicts smaller droplet sizes for the cooler vapour of the split airflow embodiment compared to vapour of non-split or total airflow embodiments. These simulation data 67 are shown in FIG. 7 for one puff at the outlet of the mouthpiece. Y-Axis represents the ratio of droplet diameters for split airflow to total airflow systems. The ratios are calculated and shown as d_split/d_ref=T*Ln(S) ref/T*Ln(S) split versus time (in seconds) during one puff on the aerosol-generating system where T is the temperature expressed in degrees Kelvin and S is the saturation ratio which is a function of Pv and $\underline{p}$ (T).

FIG. 8a is an illustration of a first heating element 30. The heating element comprises a mesh 36 formed from 304L stainless steel, with a mesh size of about 400 Mesh US (about 400 filaments per inch). The filaments have a diameter of around 16 micrometer. The mesh is connected to electrical contacts 32 that are separated from each other by a gap 33 and are formed from a copper foil having a thickness of around 30 micrometer. The electrical contacts 32 are provided on a polyimide substrate 34 having a thickness of about 120 micrometer. The filaments forming the mesh define interstices between the filaments. The interstices in this example have a width of around 37 micrometer, although larger or smaller interstices may be used. Using a mesh of these approximate dimensions allows a meniscus of aerosol-forming substrate to be formed in the interstices, and for the mesh of the heating element to draw aerosol-forming substrate by capillary action. The open area of the mesh, that is, the ratio of the area of interstices to the total area of the mesh is advantageously between 25 percent and 56 percent. The total resistance of the heating element is around 1 Ohm. The mesh provides the vast majority of this resistance so that the majority of the heat is produced by the mesh. In this example the mesh has an electrical resistance more than 100 times higher than the electrical contacts 32.

The substrate 34 is electrically insulating and, in this example, is formed from a polyimide sheet having a thickness of about 120 micrometer. The substrate is circular and has a diameter of 8 millimeter. The mesh is rectangular and has side lengths of 5 millimeter and 2 millimeter. These dimensions allow for a complete system having a size and shape similar to a convention cigarette or cigar to be made. Another example of dimensions that have been found to be effective is a circular substrate of diameter 5 millimeter and a rectangular mesh of 1 millimeter times 4 millimeter.

Figure 8C:
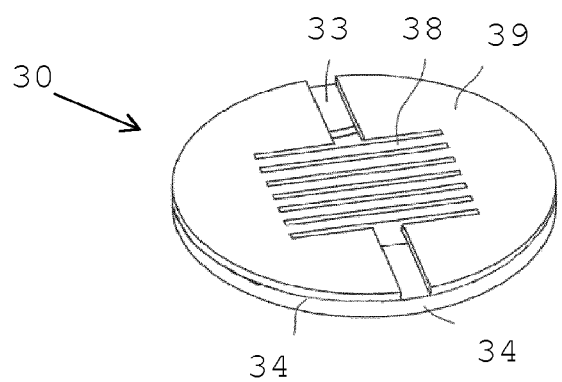

FIG. 8b and FIG. 8c are illustrations of other alternative heating elements. In the heating element of FIG. 8b the filaments 37 are bonded directly to substrate 34 and the contacts 32 are then bonded onto the filaments. The contacts 32 are separated from each other by insulating gap 33 as before, and are formed from copper foil of a thickness of around 30 micrometer. The same arrangement of substrate filaments and contacts can be used for a mesh type heater as shown in FIG. 8a. Having the contacts as an outermost layer can be beneficial for providing reliable electrical contact with a power supply.

The heating element of FIG. 8c comprises a plurality of heater filaments 38 that are integrally formed with electrical contacts 39. Both the filaments and the electrical contacts are formed from a stainless steel foil that is etched to define filaments 38. The contacts 39 are separated by a gap 33 except when joined by filaments 38. The stainless steel foil is provided on a polyimide substrate 34. Again the filaments 38 provide the vast majority of the resistance, so that the majority of the heat is produced by the filaments. In this example the filaments 38 have an electrical resistance more than 100 times higher than the electrical contacts 39.

Figures 8D, 8E, 8F:
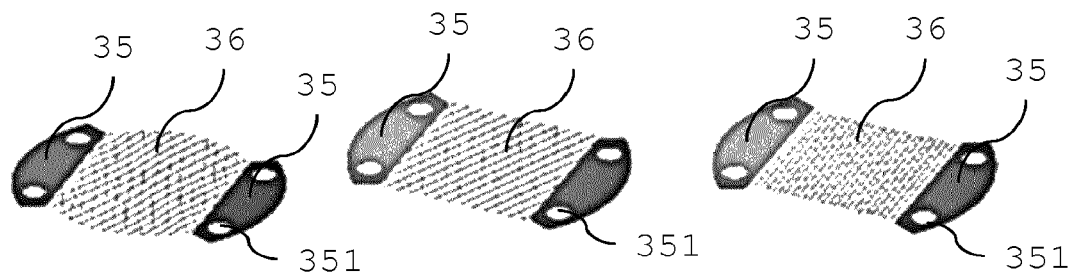

FIGS. 8d to 8e show several heating elements having a mesh 36 fixed to and between two contact portions 35. The mesh is fixed on both sides to the contact portions 35. Each contact portion has a round outer circumference and two openings 351. The heating elements 30 may be attached to the housing of a cartridge or to a supporting substrate by theses openings 351, for example by screwing.

Figures 9A, 9B:
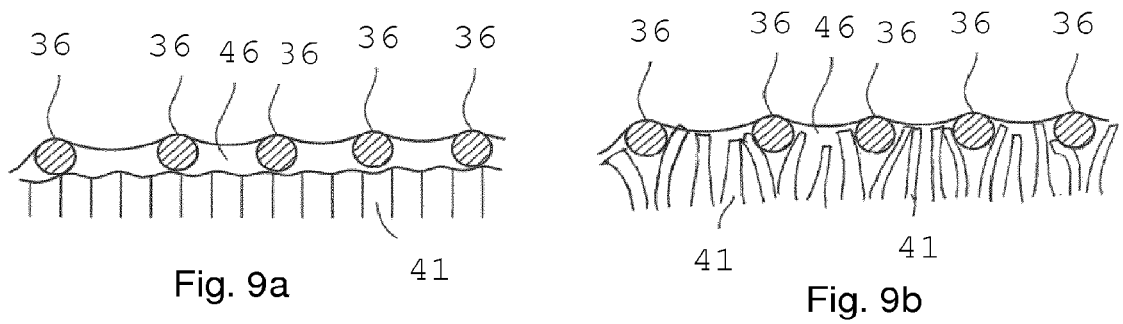
FIG. 9a, 9b are detailed views of the filaments of the heating elements, showing a meniscus of liquid aerosol-forming substrate between the filaments (FIG. 9a) and a capillary material extending between the filaments (FIG. 9b)

Capillary material 41 is advantageously oriented in the housing 4 to convey liquid to the heating element 30. When the cartridge is assembled, the heater filaments 36, 37, 38 may be in contact with the capillary material 41 and the aerosol-forming substrate can be conveyed directly to the mesh heater. FIG. 9a is a detailed view of the filaments 36 of the heating element, showing a meniscus 46 of liquid aerosol-forming substrate between the heater filaments 36. It can be seen that aerosol-forming substrate contacts most of the surface of each filament so that most of the heat generated by the heating element passes directly into the aerosol-forming substrate.

FIG. 9b is a detailed view, similar to FIG. 9a, showing an example of a capillary material 41 that extends into the interstices between the filaments 36. The capillary material 41 may be a capillary material arranged next to the or in contact with the heating element, preferably having a high temperature resistance. It can be seen that by providing a capillary material comprising fine threads of fibres that extend into the interstices between the filaments 36, transport of liquid to the filaments can be ensured.

In use the heating elements operate by resistive heating. Current is passed through the filaments 36, 37, 38, under the control of control electronics (not shown), to heat the filaments to within a desired temperature range. The mesh or array of filaments has a significantly higher electrical resistance than the electrical contacts 32, 35 and electrical connectors (not shown) so that the high temperatures are localised to the filaments. The system may be configured to generate heat by providing electrical current to the heating element in response to a user puff or may be configured to generate heat continuously while the device is in an "on" state.

Different materials for the filaments may be suitable for different systems. For example, in a continuously heated system, graphite filaments are suitable as they have a relatively low specific heat capacity and are compatible with low current heating. In a puff actuated system, in which heat is generated in short bursts using high current pulses, stainless steel filaments, having a high specific heat capacity may be more suitable.

Figure 10:
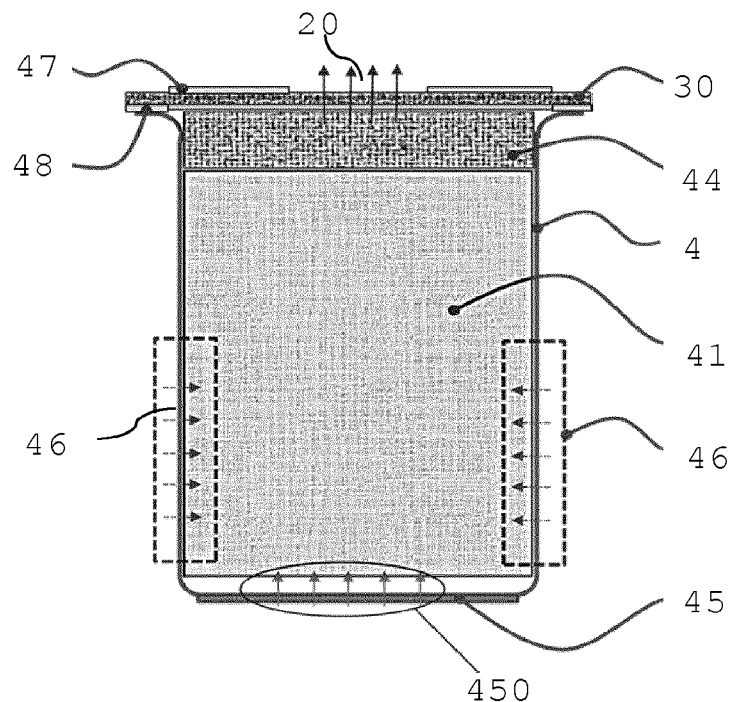
FIG. 10 shows a cross-section of a cartridge system with high retention-release material (HRM) and air passage through the HRM.

In FIG. 10 a cross section of a cartridge system, wherein a second flow route comprises an airflow directed through the cartridge is illustrated. A fluid permeable heater, for example a mesh heater 30, is provided to cover the open top of the housing 4. For sealing the top of the housing 4, a sealing layer 48, for example a polymer layer, is provided between the upper rim of the housing 4 and the heater 30. In addition, a sealing disc 47, for example a polymer disc, is provided on the top side of the heater 30. With the sealing disc 47 airflow through the heater may be controlled, in particular, airflow constraints may be provided. The sealing disc may also be arranged on the bottom side of the heater 30.

The cartridge housing 4 comprises a liquid containing high retention material or high release material (HRM) 41 serving as liquid reservoir and directing liquid towards the heater 30 for evaporation at the heater. A capillary disc 44, for example a fiber disc, is arranged between HRM 41 and heater 30. The material of the capillary disc 44 may be more heat resistant than the HRM 41 due to its closeness to the heater 30. The capillary disc is kept wet with the aerosol-forming liquid of the HRM to secure provision of liquid for vaporization if the heater is activated.

The housing 4 is provided with an air permeable bottom 45. The air permeable bottom is provided with an airflow inlet 450. The airflow inlet 450 allows air to flow through the bottom 45 into the housing in one and this direction only. No air or liquid may leave the housing through the air permeable bottom 45. The air permeable bottom 45 may for example comprise a semi-permeable membrane as airflow inlet 450 or may be a bottom cover comprising one or more one-way valves as will be shown below.

If low depression prevails on the side of the heater, as is the case during puffing, air may pass through the airflow inlet 450 into the cartridge. The airflow 20 will pass through the HRM 41 and through the heater 30. The aerosol containing airflow 20 will then flow to a downstream end of the aerosol generating device, preferably in a centrally arranged channel in a mouthpiece.

Side walls of the housing 4 may also be provided with lateral air permeable sections 46 for providing lateral airflows into the housing. Lateral air permeable sections 46 may be designed as the airflow inlets 450 in the air permeable bottom 45.

Figure 11:
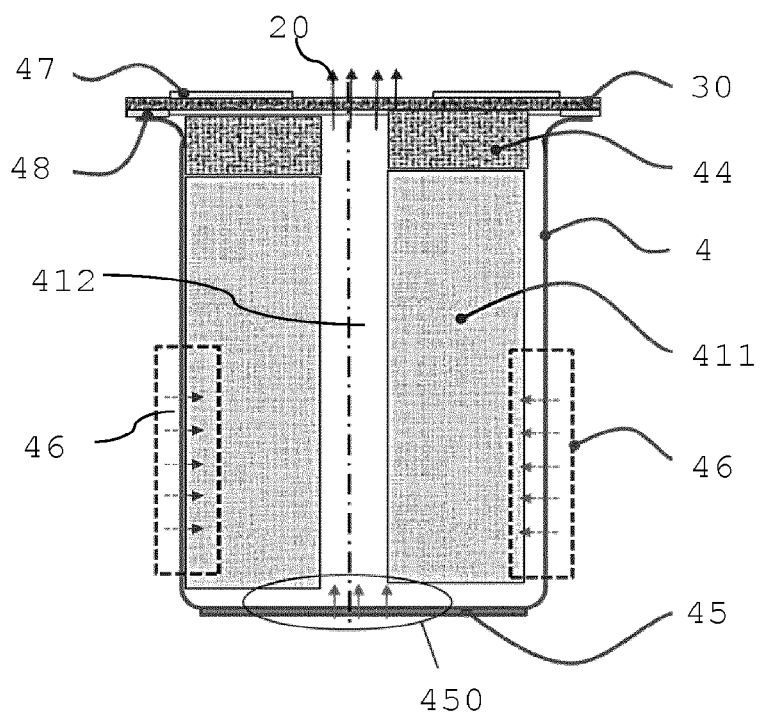
FIG. 11 shows a cross-section of another cartridge system with high retention-release material (Ham) and air passage through the cartridge.

In FIG. 11 the arrangement and function of the cartridge system is basically the same as shown in FIG. 10. However, the HRM 41 is provided with a central opening 412. Air entering the airflow inlet 450 in the bottom 45 of the housing passes through the central opening 412. The airflow passes next to the HRM in the cartridge. With optional lateral air permeable sections 46 in the side wall of the housing 4, lateral airflow may be provided through the HRM 41.

Figure 12:
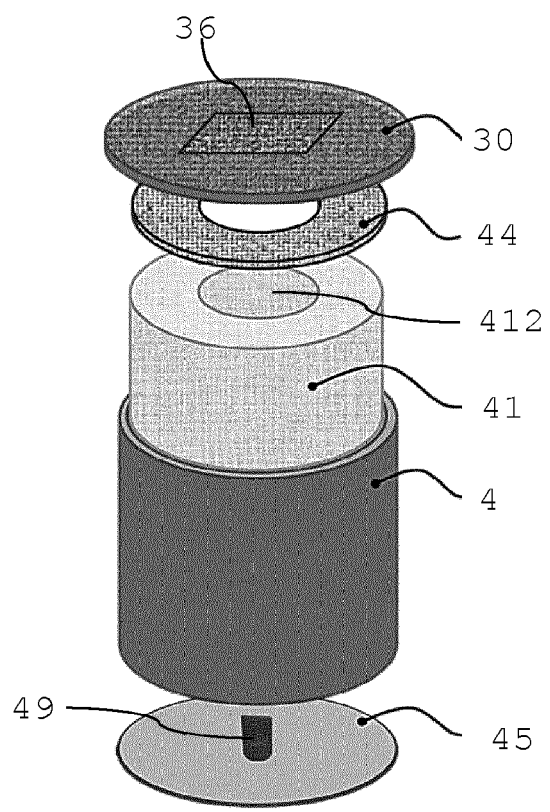
FIG. 12 shows an exploded view of the cartridge system of FIG. 11.

In FIG. 12 an exploded view of cartridge system as in FIG. 11 is shown. A ring-shaped tubular HRM 41 is provided in the housing 4. The bottom 45 of the housing is a disc comprising a one-way valve 49 arranged in the center of the disc and aligned with the central opening 412 in the HRM 41. Such a one-way valve may for example be a commercially available valve, such as for example used in medical devices or in baby bottles.

Figure 13:
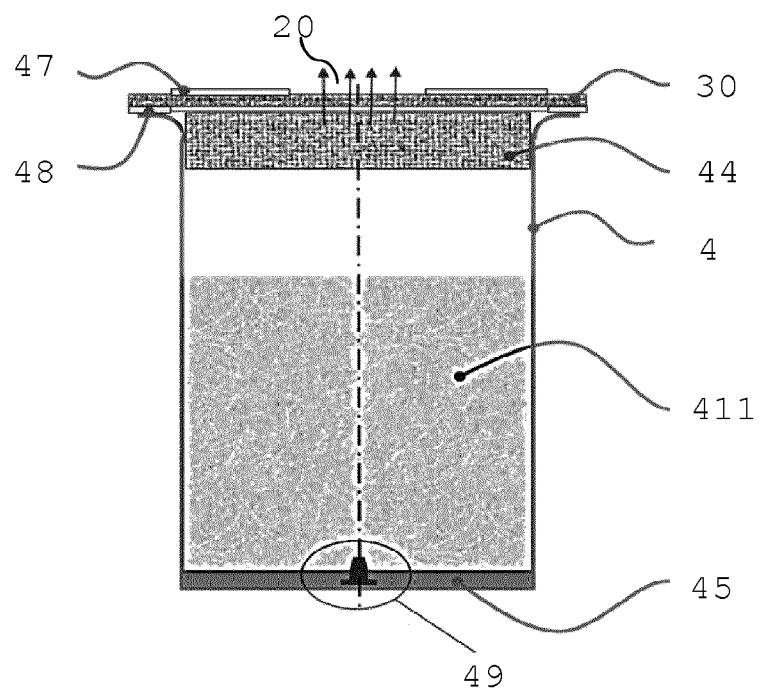
FIG. 13 shows a cross-section of a cartridge system with a liquid and air passage through the liquid.

FIG. 13 is a cross section of another embodiment of a cartridge system. Same reference numerals are used for the same or similar elements. In this embodiment, the housing 4 is filled with an aerosol-forming liquid 411. The housing may be made of metal, plastics material, for example a polymeric material, or glass. The valve 49 may directly be molded into the bottom 45 of the housing. The bottom 45 may also be provided with a cavity for air-tight assembly with the valve. Due to the valves preferably being made of a flexible material, tight assembly with the bottom material may be achieved.

In the above cartridge systems as described in FIG. 10 to FIG. 13 the cartridge housing 4 may also be a separate cartridge container in addition to the cartridge housing as described for example in FIG. 1. Especially, a liquid 411 containing cartridge is a pre-manufactured product, which may be inserted into a cartridge housing provided in the aerosol generating system for receiving the pre-manufactured cartridge.

The invention claimed is:

1. A cartridge system, comprising:
 a liquid storage portion comprising a housing configured to hold a liquid aerosol-forming substrate;
 a mouthpiece having an outlet opening at a proximal end thereof and being removably connected to a first end of the liquid storage portion; and
 a heater assembly comprising:
  an electrical heating element configured to heat the liquid aerosol-forming substrate to form an aerosol, and
  a porous capillary material comprising a ceramic or a ceramic-based material and having a first face being in physical contact with at least a portion of the electrical heating element, the porous capillary material being configured to convey the liquid aerosol-forming substrate to the electrical heating element by capillary action,
  the electrical heating element being disposed across the first face of the porous capillary material,
 wherein the liquid storage portion is disposed at a first side of the heater assembly and a first airflow channel is disposed at a second side of the heater assembly, a portion of the first airflow channel defining an airflow path that extends in a direction perpendicular to the first face of the porous capillary material and is directed at a center of the electrical heating element, and
 wherein at least a portion of a second airflow channel extends from the heater assembly to the outlet opening of the mouthpiece via a central channel of the housing.

2. The cartridge system according to claim 1, wherein said portion of the second airflow channel extends from one side of the liquid storage portion to the outlet opening of the mouthpiece via the central channel of the housing.

3. The cartridge system according to claim 1, wherein at least one lateral air permeable section is disposed along a side wall of the housing.

4. The cartridge system according to claim 1, wherein the electrical heating element comprises a filament disposed in a curved manner between two electrical contacts respectively connected to ends of the filament.

5. The cartridge system according to claim 4, wherein the filament is substantially flat.

6. The cartridge system according to claim 1, wherein the heater assembly further comprises two electrical contacts.

7. The cartridge system according to claim 6, wherein the heater assembly further comprises an electrically insulating element having an opening.

8. The cartridge system according to claim 7, wherein the two electrical contacts are supported by the electrically insulating element.

9. The cartridge system according to claim 1, wherein the electrical heating element is embedded in the porous capillary material.

10. The cartridge system according to claim 1, wherein the electrical heating element is printed onto the surface of the porous capillary material.

11. The cartridge system according to claim 1, wherein the capillary material is selected from a group consisting of a ceramic-based material of sintered powder, a fibrous material, and a combination.

12. The cartridge system according to claim 1, wherein the capillary material is in fluid connection with the liquid aerosol-forming substrate.

13. The cartridge system according to claim 1, further comprising an airflow inlet disposed proximal to a bottom of the heater assembly.

14. The cartridge system according to claim 1, further comprising:
 an electrically insulating element having an opening; and two electrical contacts respectively connected to ends of the electrical heating element, the two electrical contacts being supported by the electrically insulating element.

15. The cartridge system according to claim 14, wherein the heater assembly is configured to be continuously heated.

16. The cartridge system according to claim 14, wherein the heater assembly is configured to be heated in bursts with pulses of electrical current.

17. The cartridge system according to claim 1, wherein the capillary material is configured to be kept wet by the liquid aerosol-forming substrate.

18. The cartridge system according to claim 4, wherein the heater assembly has a substantially flat orientation, such that a common plane passes through the filament.

19. The cartridge system according to claim 1, wherein the capillary material provides thermal isolation from the electrical heating element.

20. The cartridge system according to claim 19, wherein the capillary material protects the liquid aerosol-forming substrate in the liquid storage portion from decomposition.

\* \* \* \* \*